United States Patent [19]
Fry-Welch et al.

[11] Patent Number: 5,163,443
[45] Date of Patent: Nov. 17, 1992

[54] SYSTEM FOR TESTING HAND, WRIST, AND FOREARM STRENGTH

[75] Inventors: Donna Fry-Welch, Ann Arbor; Lucinda Pfalzer, Flint; Henry C. Kowalski, Grand Blanc, all of Mich.

[73] Assignees: University of Michigan, Ann Arbor; GMI Engineering and Management Institute, Flint, both of Mich.

[21] Appl. No.: 739,054

[22] Filed: Aug. 1, 1991

[51] Int. Cl.$^5$ .............................................. A61B 5/103
[52] U.S. Cl. ...................................... 128/782; 73/379
[58] Field of Search .................. 128/774, 782; 33/511, 33/512, 515; 73/379–381, 865.4

[56] References Cited

U.S. PATENT DOCUMENTS

| | | | |
|---|---|---|---|
| 4,436,099 | 3/1984 | Raftopoulos | 128/782 |
| 4,774,966 | 10/1988 | Lemmen | 73/379 |
| 4,834,057 | 5/1989 | McLeod | 128/782 |
| 5,016,874 | 5/1991 | Boardman | 272/135 |
| 5,050,618 | 9/1991 | Larsen | 128/782 |

OTHER PUBLICATIONS

Little et al., "Wrist and Shoulder Analyzer", Research Disclosure, Nov. 1981.

Primary Examiner—Max Hindenburg
Attorney, Agent, or Firm—Rohm & Monsanto

[57] ABSTRACT

A system for measuring the forces which are applied by a limb of a living being, particularly the hand, wrist, and forearm of a human being, employs a plurality of cable members for conducting the forces exerted in a variety of directions to a single force transducer. In addition to permitting a significant reduction in cost for the apparatus of the invention, the use of a single transducer ensures that all forces are correlated in magnitude with respect to one another, thereby greatly reducing the problems associated with system calibration. The apparatus aspect of the invention permits readings of plural motions and forces to be taken, which readings can be delivered to a recording device, such as a computer for storage, analysis, and cross-correlation of the resulting data with itself and with extrinsic data. The invention therefore is useful in determining the presence of cumulative trauma disorders, such as carpal tunnel syndrome, and can assist in identifying individuals and groups of individuals, illustratively on the basis of job function, which are at high risk of developing this condition.

17 Claims, 3 Drawing Sheets

SYSTEM FOR TESTING HAND, WRIST, AND FOREARM STRENGTH

BACKGROUND OF THE INVENTION

This invention relates generally to systems for measuring forces and more particularly, to a system which mesures forces applied by a limb of a living being in a plurality of directions using only a single force transducer.

Cumulative trauma disoders are being reported with increasing frequency in industrial settings. One such cumulative trauma disorder is Carpal Tunnel Syndrome, which is characterized by decreased median nerve conduction velocities; decreased sensation in the palm, thumb, index, or middle fingers; decreased strength; pain; and swelling. Inflammation of tendons in the wrist resulting in swelling can compress the median nerve causing the resultant changes in sensation, strength and pain. One reason for the increase in the reporting of cumulative trauma disorders, particularly Carpal Tunnel Syndrome is that the increasing mechanization of industry requires workers to perform more repetitive work. It is the repetitive nature of the work which contributes to the cumulative trauma disorders.

There is a need for a reliable, portable, and inexpensive apparatus and system for measuring muscle force for assessing maximal force, percent of maximal force, and force curves during wrist and forearm motions. The force measures are then correlated with the forces required in specific work tasks, lifestyle, psycho-social factors, and other physiological factors which contribute to the manifestation of Carpal Tunnel Syndrome.

In addition to ascertaining whether one has a cumulative trauma disorder, there is also a need for a system which assists in identifying persons at higher risk for developing such disorders, particularly Carpal Tunnel Syndrome. Preferably, such a system should be useful in the acquisition of information pertaining to:

1. Maximal and submaximal wrist forces, including flexion, extension, radial deviation, and ulnar deviation;
2. Maximal and submaximal forearm forces, including supination and pronation;
3. Wrist and hand nerve conduction velocity studies;
4. Correlation of the foregoing measures with wrist and hand sensation, range of motion, and flexibility;
5. Correlation of the foregoing measures with the information acquired by the Carpal Tunnel Syndrome employee assessment system, which includes information such as:
   a. personal demographic characteristics;
   b. current work tasks and past work tasks;
   c. prior medical conditions and injuries;
   d. current symptons possibly associated with work tasks;
   e. employee perception of pain;
   f. lifestyle patterns;
   g. current medical conditions and associated medications;
   h. past and present exercise routines;
   i. hobbies and outside of work activities; and
   j. work satisfaction.

In order to identify work site-related factors which may contribute to cummulative traumma disorders or aggravate existing symptons associated with Carpal Tunnel Syndrome, it may be useful to compare wrist and forearm forces required to perform a work task with the employees' ability to generate maximal and submaximal wrist and forearm forces. It may additionally be useful to compare, on specific work tasks, force curves of experienced or skilled workers, in contrast to those of new employees.

It is, therefore, and object of this invention to provide a simple and inexpensive system for measuring multiple types of forces and torques producible by a limb of a living being.

It is another object of this invention to provide a system which can readily produce signals repesentative of the various forces or loads which can be applied by a limb of a living being, the forces being readily correlatable to one another.

It is also an object of this invention to provide a method and apparatus for measuring and evaluating the strength and ability of movement of a limb or upper extremity of a living being wherein the data is easily supplied to a computer.

It is a further object of this invention to provide a limb strength and mobility monitoring system which is easily transportable to a work place.

It is additionally an object of the invention to provide a force mesurement system for assessing the nature and extent of cumulative trauma disorders, which easily can be calibrated.

It is yet a further object of this invention to provide a strength measurement system which can measure grip strength and finger strength.

It is also another object of this invention to provide a dynamometer system which can perform all of the necessary strength tests asssociated with the forearm, wrist, and hand.

SUMMARY OF THE INVENTION

The foregoing and other objects are achieved by this invention which provides a system for measuring a force applied by the limb of a living being along any of a plurality of directions. In accordance with the invention, first and second support members are arranged on opposite side of the limb. A transducer is provided for producing a perceptible or measurable signal, illustratively electrical in nature, responsive to a force applied thereto. First and second cables, each having a first end disposed in the vicinity of a respectively associated one of the first and second support members, and a second end arranged in the vicinity of the transducer, are provided for conducting the force being measured. The first and second flexible cables are coupled to the transducer via a unidirectional coupler or yoke. A limb coupling arrangement, which may be in the form of a harness, handle, or band, is coupled to at least one of the flexible cables so that a force generated by the limb is transmitted to the transducer.

In one embodiment of the invention, the limb coupling arrangement is in the form of a harness, or band, arranged to surround the limb. A removable link couples the harness to the first end of at least one of the first and second flexible cables.

In another embodiment of the invention, a rotary device is provided for measuring a torque applied by the limp of a living being. The rotary device may be in the form of a rotatable member with a handle coupled thereto affixed to an intermediate support, and couled to at least one of the flexible cables. The handle on the rotary device may also measure positioning, isometric grip and pinch strength.

A limb support is provided for positioning and supporting the limb of the patient being tested at a predetermined location between the first and second support members, and in a predetermined orientation to facilitate the examination.

In a still further embodiment of the invention, third and fourth support members are arranged on opposite sides of the limb, and generally may be arranged substantially orthogonal with respect to the first and second support members. Third and fourth flexible cables are provided, each having a first end disposed in the vicinity of a respectively associated one of the third and fourth support members, and a second end coupled to the unidirectional coupler or yoke. Thus, in this embodiment, all four flexible cables conduct their force, when in tension, to the unidirectional coupler. As previously stated, the unidirectional coupler is coupled to the transducer, such that all the forces received by any of the cables in tension are delivered to the single transducer, thereby eliminating the need for multiple transducers, and the calibration and correlation problems associated therewith.

The method of determining forces applied by a limb of a living being includes the steps of:

(1) first coupling the limb of the living being to a first flexible line (e.g., cable);
(2) moving the limb of the living being so as to apply a tensile force onto the first flexible line;
(3) transmitting the tensile force via the first flexible line to a transducer; and
(4) producing a signal responsive to the tensile force.

In one embodiment of the method aspect of the invention, the limb of the living being is connected to a second flexible line. The step of transmitting the tensile force to the transducer is performed by one of the thus connected flexible lines. In operation, the flexible lines are coupled to a coupler unit or yoke which operates in a unidirectional manner. More specifically, only the flexible line (or cable) having the tensile load thereon, in this embodiment, will produce an effect on the transducer.

The limb of the living being is applied to a rotary coupling element, via a handle, which is coupled to the first flexible line. The rotary coupling element is manipulable by the living being, and the torque applied thereto is transmitted as a tensile force to the transducer. The transducer will then issue a signal which is responsive to the tensile force. In certain embodiments, the tensile force is stored in a memory, such as the memory of a computer, for analysis with respect to other data obtained from the transducer, or supplied to the computer by other means. The handle may also be used to test isometric grip and pinch strength.

In accordance with a further system aspect of the invention, a plurality of cord-like members, which in some embodiments of the invention may be cables, are employed to conduct tensile forces corresponding to a respectively associated plurality of directions. The cord-like members are coupled to a transducer which produces a signal responsive to the force applied thereto. There is further provided an interface whereby the living being can cause a tensile force to be applied to at least one of the plurality of cord-like members. The strength with which the interface is manipulated causes a corresponding increase in the force registered by the transducer. As previously indicated, the initial force applied by the living being may be of any of a plurality of types, such as a linear force or a torque.

This system additionally employees a plurality of support means, each of which is associated with respective direction of force applied by the living being. In a specific illustrative embodiment of the invention, the support members are arranged to form an open frame structure.

BRIEF DESCRIPTION OF THE DRAWING

Comprehension of the invention is facilitated by reading the following detailed description, in conjunction with the annexed drawing in which.

DETAILED DESCRIPTION

Figure 1:
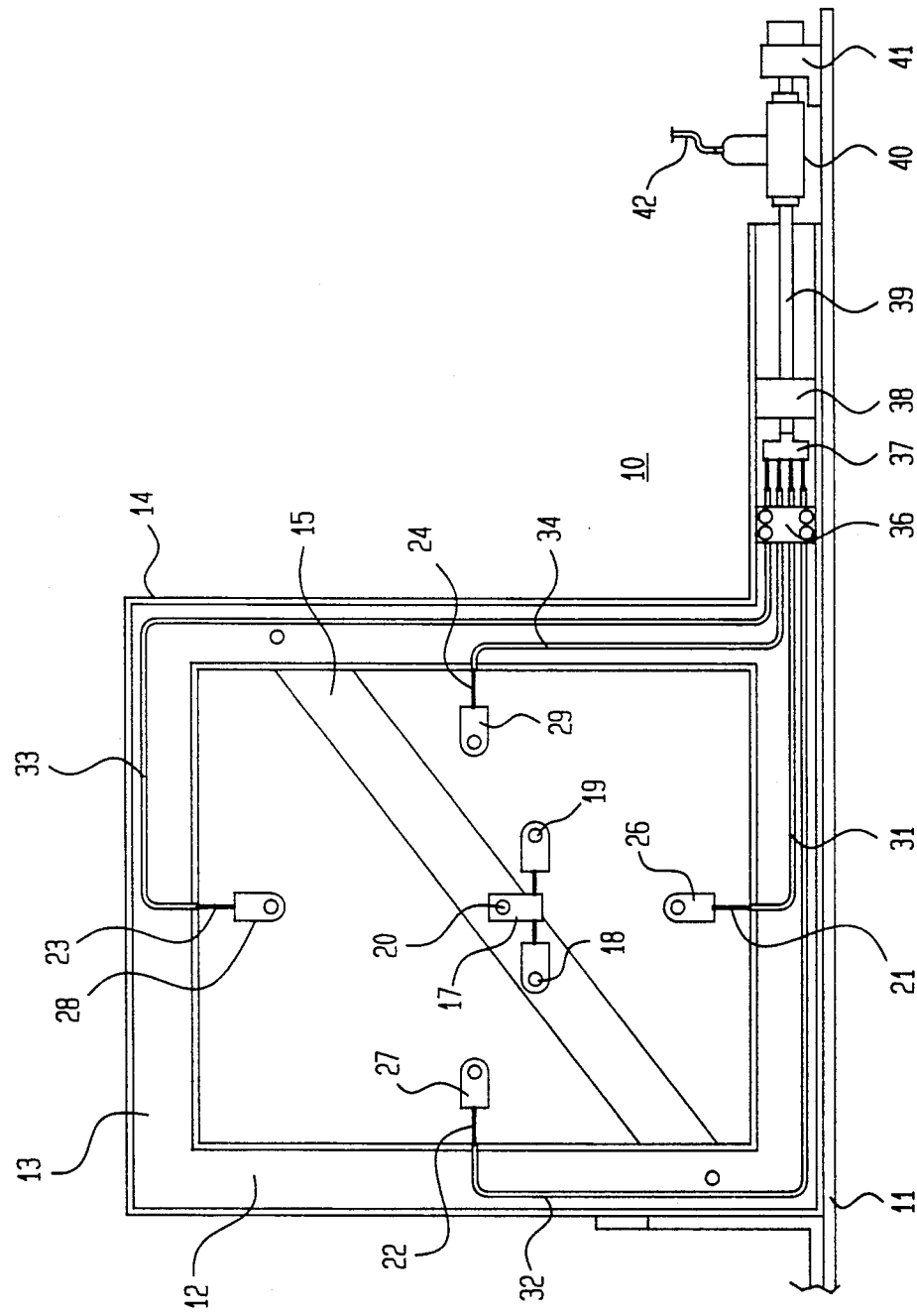
FIG. 1 is a simplified schematic illustration of an arrangement which is useful for determining the presence of cumulative trauma disorders, constructed in accordance with the principles of the invention.

FIG. 1 is a partially schematic simplified representation of a specific illustrative embodiment of the invention. The figure shows a dynamometer system 10 which generally is formed of four support members, designated as 11, 12, 13, and 14. In this embodiment, support members 11-14 are arranged to form a rectangular open frame structure. In addition, dynamometer syste 10 is provided with a cross support member 15 which is shown to be coupled to support members 12 and 14.

Cross support member 15 has installed thereon a rotary element 17 which has associated therewith two coupling portions, 18 and 19, and which is arranged to be rotatable about a pivot 20. As will be described below with respect to FIG. 3, rotary element 17 is used to evaluate the ability of the testee to exert a torque. In addition, as previously indicated, cross support member 15 is easily removable off of support members 12 and 14 so as to permit the dynamometer system to be used for other types of measurements.

Figure 2:
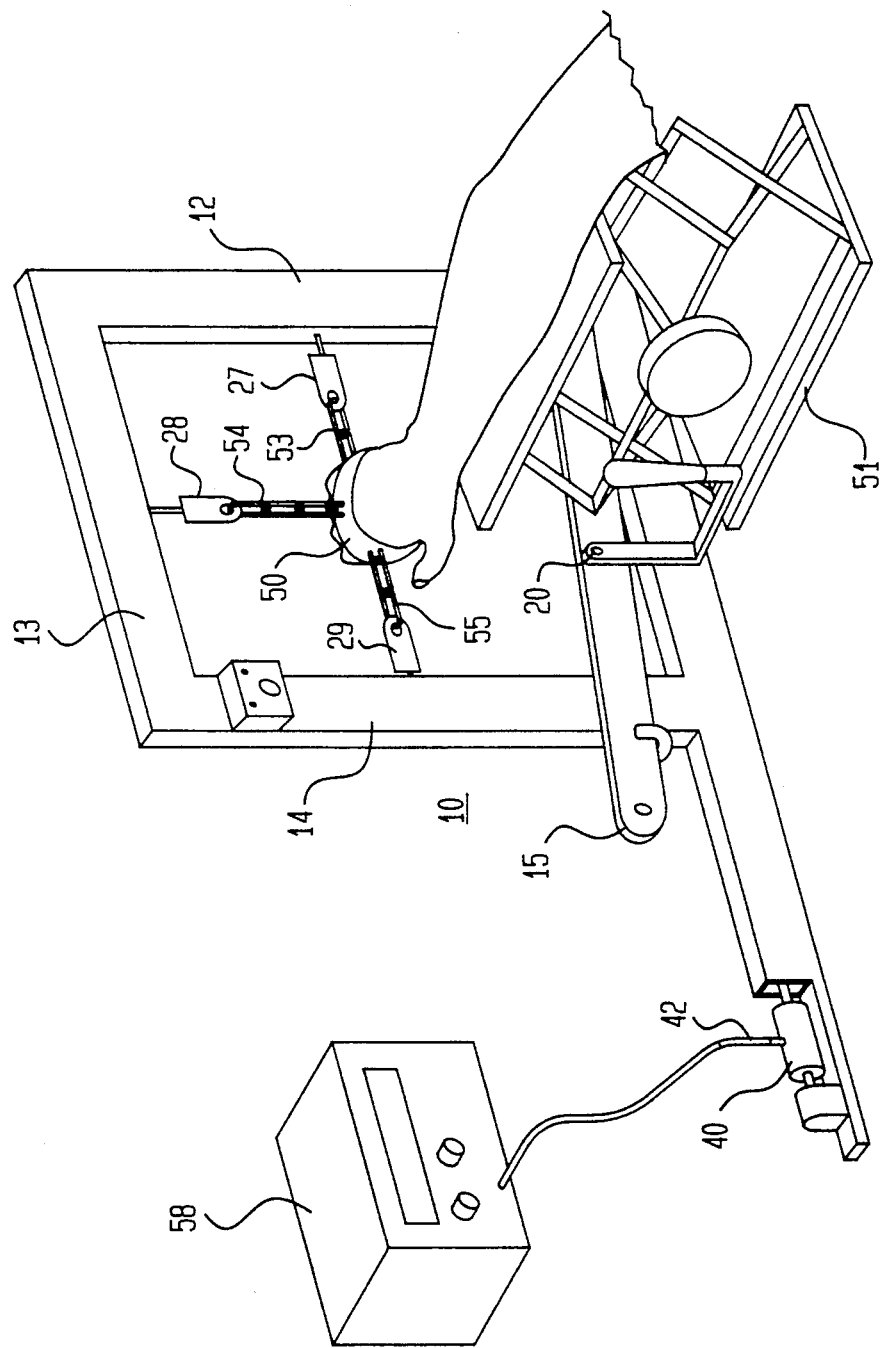
FIG. 2 is a simplified representaion of the embodiment of FIG. 1 illustrating the manner in which the arrangement is interfaced with the arm of a human being.

FIG. 2 is a simplified representation of the embodiment of the invention for performing partially isometric strength tests shown in FIG. 1 and, as shown, has cross support member 15 removed therefrom. For purposes of the evaluation shown in FIG. 2, the cross support member is not entirely removed but instead is simply released from support member 14 and is permitted to pivot out of the way.

Referring once again to FIG. 1, it is seen that the dynamometer system is provided with four cord-like elements designated as cables 21, 22, 23, and 24. Each of cables 21-24 is associated with a respective one of support members 11-14. In addition, each such cable is terminated at a first end which is disposed within the open frame structure of the dynamometer system with a respective one of cable terminations 26, 27, 28, and 29.

Each of cables 21-24 is installed within a cable sheath, the cable sheaths being designated in the figure as 31, 32, 33, and 34. The four cables of the present embodiment, and their respectively associated cable sheaths are brought to a clamping block 36 which holds cable sheaths 31-34, but otherwise does not restrict the cables therewithin to move axially. The four cables 21-24 are each engaged with a coupler 37 which is coupled to a transducer 40. Such coupling is achieved via a shaft 39 which is held in place by a shaft support 38. The distal end of transducer 40 is supported by a transducer support block 41.

In the specific illustrative embodiment described herein, cables 21-24 are flexible and, as stated, are movable within their cable sheaths. However, the cables in this embodiment remain taut within their respective cable sheaths. Thus, force is transmitted through the cables, but there is not necessarily present any displacement of the cables within the cable sheaths or with respect to clamping block 36 upon the application of the forces described herein.

Transducer 40 produces, in this embodiment, an electrical signal which corresponds to the tensile force of any of cables 21-24, applied at coupler 37. Coupler 37 is unidirectional in its operation in that it will conduct a tensile force from any of the cables along coupler shaft 39 to the transducer, but will not be responsive to any compression forces in the cables.

FIG. 2 shows the forearm and wrist of a testee disposed within a harness 50, which is in the form of a band. The forearm of the testee is permitted to rest upon a support 51, which in this specific illustrative embodiment, in an ordinary laboratory jack. Harness 50 is coupled to cable terminations 27, 28, and 29 via respective coupling links 53, 54, and 55. Thus, as the testee flexes his wrist, an appropriate tensile force is placed on the cables which transmit the force to transducer 40.

As shown in this figure, transducer 40 is coupled at output terminal 42 to a readout device 58 which, in certain embodiments, can have a memory for storing data corresponding to the output signals of transducer 40. In other embodiments, transducer 40 may be connected directly to a computer (not shown) for storing and correlating the data obtained from the transducer. In addition, the data obtained from the transducer can be combined with extrinsic data, such as data corresponding to population norms and characteristics, work place accidents, etc.

In other embodiments of the invention, other interface devices, such as a split handle (not shown), can be utilized to achieve other measurements. Persons of skill in the art would be able to configure an arrangement which permits the present invention to be utilized to measure pinch and grip strengths.

Figure 3:
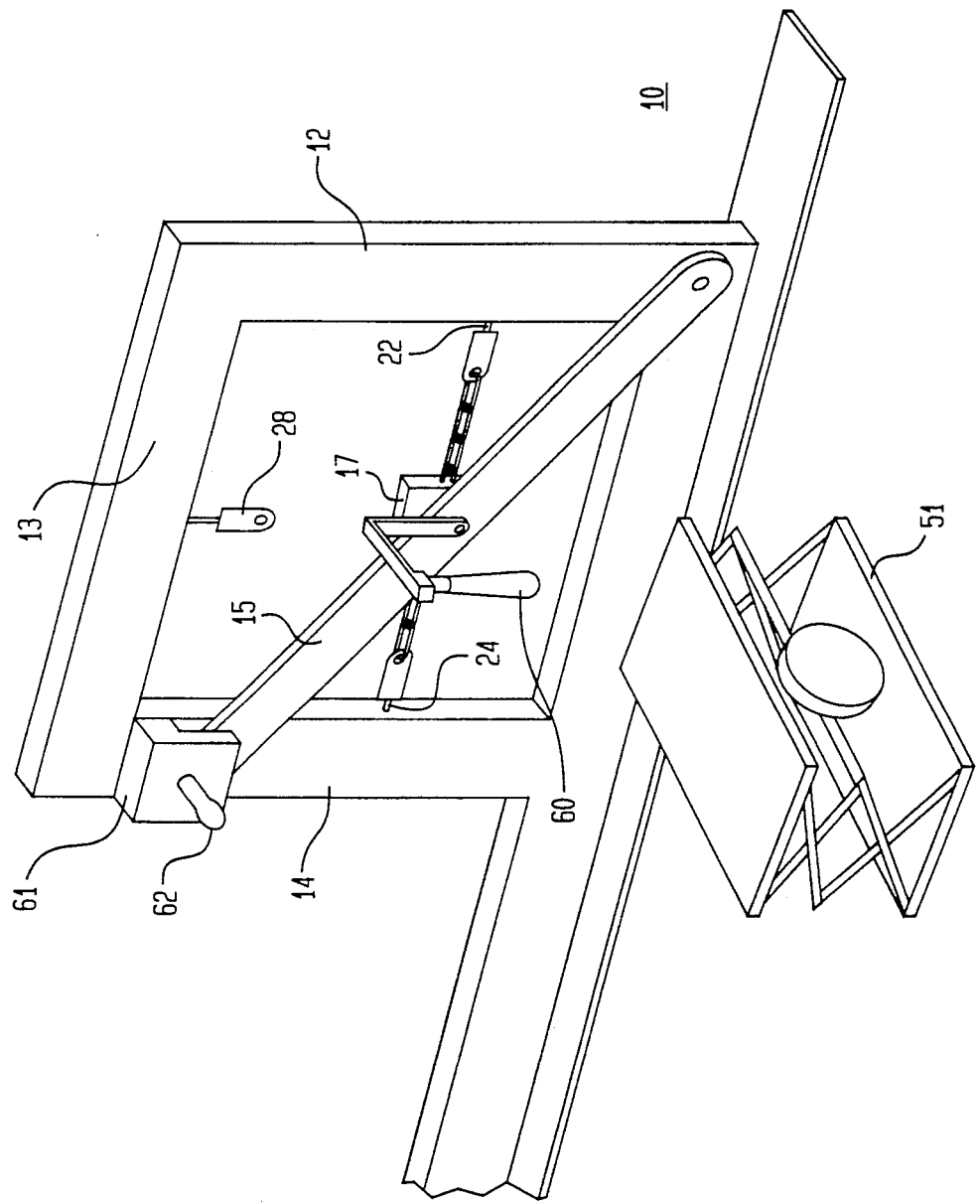
FIG. 3 is a simplified representation of the embodiment of the invention adapted to be responsive to torque forces applied by a testee.

FIG. 3 is a representation of the embodiment of the invention discussed hereinabove, showing the rotary element 17 coupled via respective coupling links to the cable terminations. As the testee (not shown in this figure) applies a rotative force to the handle 60 of the rotary element, a tensile force is applied to one of cables 22 and 24, which registers the force, in the form of a corresponding electric signal at output terminals 42 of the transducer (not shown in this figure). In this figure, cross support member 15 is shown in a raised position, it being retained by engagement with a locking block 61 mounted on support member 14, with a pin 62 therethrough.

Although the invention has been described in terms of specific embodiments and applications, persons skilled in the art can, in light of this teaching, generate additional embodiments without exceeding the scope or departing from the spirit of the claimed invention. For example, persons of skill in the art would be able to configure the system of the present invention to achieve measurements which are not explicitly set forth herein but nevertheless are within the scope of the present invention. Such additional embodiments may include, without limitation, arrangements for measuring hand pinch strength and isometric grip strength, and adaptations for performing measurements which pertain to other limbs. Accordingly, it is to be understood that the drawing and description in this disclosure are proffered to facilitate comprehension of the invention, and should not be construed to limit the scope thereof.

What is claimed is:

1. A system for measuring a force applied by the limb of a living being along any of a predetermined plurality of directions of applications of the force, the system comprising:

first and second support means arranged on opposite sides of the limb;

transducer means for producing a signal responsive to a substantially static force applied thereto;

first and second flexible line means each having a first end disposed in the vicinity of a respectively associated one of the first and second support means, and a second end arranged in the vicinity of said transducer means, said first and second flexible line means being axially substantially inextensible and associated with respective first and second directions of application of the force by the limb of the living being;

coupler means for coupling said second ends of at least said first and second flexible line means to said transducer means such that substantially static tensile forces in said first and second flexible line means are delivered to said transducer means; and limb coupling means for coupling said first and second flexible line means to the limb, whereby a substantially static tensile force in said coupled one of said first and second flexible line means is delivered to said transducer means.

2. The system of claim 1 wherein said limb coupling means comprises a harness installed on the limb of the living being.

3. The system of claim 2 wherein there is further provided a link member for coupling said harness to said at least one first end of said first and second flexible line means.

4. The system of claim 3 wherein there is further provided a second link member for coupling said harness to the other first end of said first and second flexible line means.

5. The system of claim 1 wherein said limb coupling means comprises rotary means for measuring a torque applied by the limb of the living being.

6. The system of claim 5 wherein there is further provided an intermediate support means arranged intermediate of said first and second support means for supporting said rotary means.

7. The system of claim 1 wherein there is further provided limb support means for supporting the limb of the living being at a predetermined location and in a predetermined orientation with respect to said first and second support means.

8. The system of claim 7 wherein said predetermined location where the limb of the living being is supported by said limb support means is intermediate of said first and second support means.

9. The system of claim 1 wherein there are further provided:

third and fourth support means arranged on opposite sides of the limb, said third and fourth support means being arranged substantially orthogonal to said first and second support means; and third flexible line means having a first end disposed in the vicinity of a respectively associated one of the third support means, and a second end coupled to said coupler means, said third flexible line means being axially substantially inextensible.

10. A method of determining forces applied by a limb of a living being, the method comprising the steps of:

first coupling the limb of the living being to a first flexible line, said first flexible line being substantially inextensible and associated with a first direction of application of a force by the limb of the living being;

second coupling the limb of the living being to a second flexible line, said second flexible line being substantially inextensible and associated with a second direction of application of force by the limb of the living being;

urging the limb of the living being in a predetermined direction so as to apply a substantially static tensile force onto a selected one of the first and second flexible lines;

transmitting the substantially static tensile force via the selected one of the first and second flexible lines to a transducer to which the first and second flexible lines are coupled; and producing a signal responsive to the substantially static tensile force.

11. The method of claim 10 wherein said step of transmitting is performed via a coupler which couples the first and second flexible lines to the transducer.

12. The method of claim 10 wherein said step of first coupling is performed via a rotary coupling element which is coupled to the first flexible line, and said step of urging comprises the step of urging rotatively at least a portion of the limb of the living being.

13. The method of claim 10 wherein there is further provided the step of capturing the signal responsive to the substantially static tensile force.

14. The method of claim 13 wherein there is further provided the step of storing in a memory information corresponding to the signal responsive to the substantially static tensile force.

15. A system for determining the presence of cumulative trauma disorders in a living being, the system comprising:

a plurality of cord-like means for conducting substantially static tensile forces corresponding to a respectively associated plurality of directions, each of said cord-like means being substantially inextensible and each being associated with a predetermined direction of application of a substantially static tensile force applied by the living being;

transducer means for producing a signal responsive to a substantially static force applied thereto by any one of the plurality of cord-like means;

coupler means for coupling said plurality of cord-like means to said transducer means such that the substantially static tensile forces conducted by said plurality of cord-like means are delivered to said transducer means; and living being interface means for connecting the living being to at least one of said plurality of cord-like means, whereby a tensile force in said coupled one of said plurality of cord-like means is delivered to said transducer means.

16. The system of claim 15 wherein there is further provided a plurality of support means arranged with respect to one another to be associated with a respective direction of the substantially static force applied by the living being.

17. The system of claim 15 wherein said plurality of support means are arranged to form an open frame structure.

* * * * *